United States Patent [19]

Totani et al.

[11] Patent Number: 4,902,797
[45] Date of Patent: Feb. 20, 1990

[54] AMMINE-ALICYCLIC AMINE-PLATINUM COMPLEXES AND ANTITUMOR AGENTS

[75] Inventors: Tetsushi Totani, Hyogo; Katsutoshi Aono, Nara; Yasuko Adachi, Osaka, all of Japan

[73] Assignee: Shionogi & Co., Ltd., Fukushima, Japan

[21] Appl. No.: 135,061

[22] Filed: Dec. 18, 1987

[30] Foreign Application Priority Data

Dec. 18, 1986 [JP] Japan .................................. 61-303529

[51] Int. Cl.[4] ................... A61K 31/555; C07D 295/22
[52] U.S. Cl. ...................................... 546/11; 548/402; 548/950; 548/955; 540/465; 540/541
[58] Field of Search .......................... 546/11; 548/402; 540/465, 541

[56] References Cited

PUBLICATIONS

Hoeschele, Chem. Abs. 78, 105899p, (1973).
Simon, Chem. Abst. 87, 145547q, (1977).
Tobe, I., Chem. Abs. 86, 182963x, (1977).
Conners, Chem. Abst., 78, 79753q, (1972).
Tobe II, Chem. Abst. 80, 55897e, (1973).
Pazdur, Proc. Am. Soc. Clin. Oncology, vol. 3, p. 219, (1984).
Schabel, Jr. Pharmac. Ther A., vol. 1, pp. 411–435, (1977).
Braddock, Chem. Abst. 83, 141759e.

*Primary Examiner*—Mark L. Berch

[57] ABSTRACT

A compound of the formula (I):

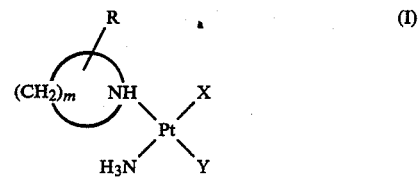

(wherein R is $C_1$–$C_6$ alkyl, hydroxy, carboxy, $C_1$–$C_6$ alkoxy, halogen or oxo; m is an integer from 2 to 7; X and Y each is chlorine or nit-rato ligand, or taken together form —OCOCH($R^1$)O—, OCOCOO—,

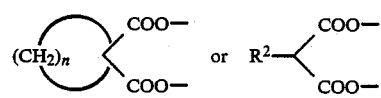

$R^1$ is hydrogen, $C_1$–$C_5$ alkyl, hydroxymethyl, halogmethyl or phenyl; $R^2$ is hydrogen or $C_1$–$C_5$ alkyl; and n is an integer from 2 to 5), being useful as antitumor agents is provided.

2 Claims, No Drawings

AMMINE-ALICYCLIC AMINE-PLATINUM COMPLEXES AND ANTITUMOR AGENTS

BACKGROUND OF THE INVENTION

1. Field of the Invention

This invention relates to novel ammine-alicyclic amine-platinum complexes which show potent antitumor activities with low toxicity.

2. Description of the Prior Art

There are known several platinum compounds having anti-tumor activities. For example, cisplatin (Bristol Myers) and carboplatin (Bristol Myers) are reported as having such activities. The present inventors have intensively investigated to find the platinum compounds which have more potent antitumor activities with less toxicity than the prior art compounds. So the inventors tried to find improved compounds with antitumor acitivities and selected some compounds, for example, diglucuronato-cis-diammine-platinum (II) (U.S. Pat. No. 457550) and (trans-dihydroxo)(glycolato-0,0')(diammine)platinum (IV) (U.S. Pat. No. 4658048).

SUMMARY OF THE INVENTION

This invention relates to the ammine-alicyclic amine-platinum complexes. More particularly, it relates to a compound of the formula (I):

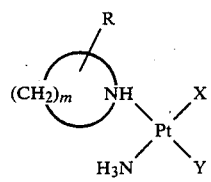

(wherein R is $C_1$–$C_5$ alkyl, hydroxy, carboxy, $C_1$–$C_5$ alkoxy, halogen or oxo; m is an integer from 2 to 7; X and Y each is chlorine or nitrato ligand, or taken together form —OCOCH($R^1$)O—,

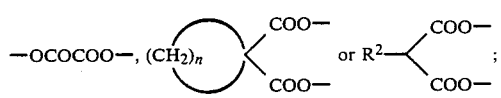

$R^1$ is hydrogen, $C_1$–$C_5$ alkyl, hydroxymethyl, halomethyl or phenyl; $R^2$ is hydrogen or $C_1$–$C_5$ alkyl; and n is an integer from 2 to 5).

The said compound is prepared in accordance with the undermentioned scheme.

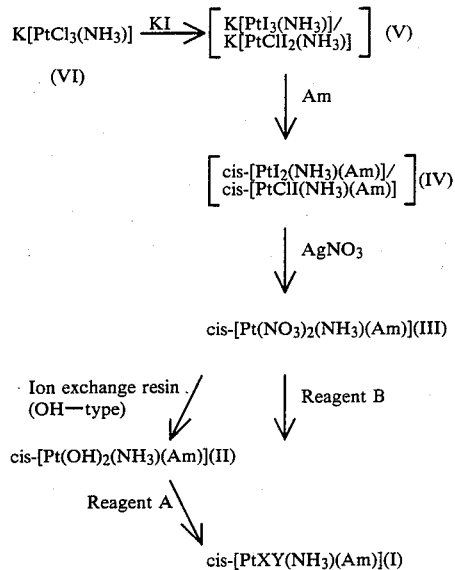

(wherein Am is

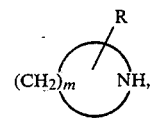

and R, m, X and Y each has the same significance as defined above. The reagent A includes HOOCCH($R^1$)OH, $(COOH)_2$,

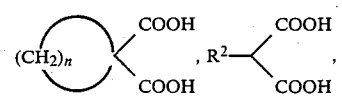

and HCl.

The reagent B includes alkali metal salts of reagent A above illustrated.

In this reaction scheme, the compound (V) can be prepared by reacting the compound (VI) with 5 to 45 mol equivalent of potassium iodide in water at room temperature for 30 minutes. When 3 mol equivalent of potassium iodide is used, some complicated products are obtained. An excessive amount (15 mol equivalent) of potassium iodide gives a mixture of $K[PtI_3(NH_3)]$ and $K[PtClI_2(NH_3)]$ and the ratio of both compounds can be calculated from the elemental analysis.

Aqueous solution of alicyclic amine in an amount of same mol equivalent to the starting material (VI) is added to a solution of the compound (V), and the mixture is allowed to react at room temperature for 0.5 to 1 hour, whereby a mixture (VI) of the compound of X=Y=Iodine and the compound of one of X and Y being Iodine and other=Chlorine in the formula (I) is obtained.

Then the compound (III) is prepared by reacting the compound (IV) with 2 mol equivalent of silver nitrate in water with shielding light. The compound (III) contains two nitrato groups in place of two halogens.

The compound (II) in which two nitrato groups are replaced by hydroxy groups can be prepared by passing aqueous solution of the compound (III) through a column filled with an anion exchange resin (OH-type) such as Amberlite IRA-400, Dowex I or Diaion SA-10A. Since the compound (II) is instable in solid form, it is generally preferred to use the resultant solution in the subsequent step without purification.

The compound (II) is dissociated in aqueous solution as shown below and shows alkalinity.

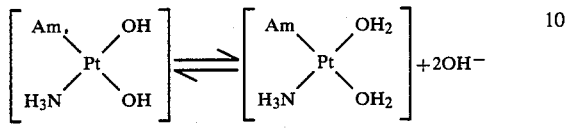

Aqueous solution of the compound (II) is allowed to react with an equimolar amount of the reagent A to give the compound (I). Since this reaction proceeds quantitatively, the reagent A may be used in an amount equimolar to the Compound (III). The present reaction is usually carried out at room temperature and terminates within 10 days; if necessary, the reaction may be conducted at 50°–70° C. The terms used in the above definition will be illustratively explained below.

The terms "$C_1$–$C_5$ alkyl" herein employed refers to a straight or branched saturated alipatic hydrocarbon group such as methyl, ethyl, n-propyl, n-butyl, isobutyl, sec-butyl, tert-butyl, n-pentyl and neo-pentyl.

The terms "$C_1$–$C_5$ alkoxy" represents methoxy, ethoxy, n-propoxy, isopropoxy, n-butoxy, isobutoxy, sec-butoxy, tert-butoxy, n-pentyloxy and sec-pentyloxy.

The terms "halomethyl" represents methyl groups binding 1-3 halogen atoms such as fluorine, chlorine and bromine.

The compounds (I) of the present invention can be administered to humans or animals enterally or parenterally. For example, the compounds (I) of the present invention dissolved or suspended in solvents for injection (e.g. distilled water for injection, physiological saline, 5% aqueous glucose solution, aqueous ethanol, aqueous glycerin, aqueous propylene glycol, etc.), can be administered intravenously, intramuscularly, or subcutaneously, or by means of instillation.

The compounds of the present invention may be placed in closed ampoules as a solution or suspension, and more preferably preserved in ampoules or vials in forms of crystals, powders, fine crystals, lyophilizate, so as to be dissolved immediately before use. Stabilizer may also be added.

When the compounds (I) of the present invention are used in the treatment of tumors of adults, they are enterally and parenterally administered at a dose or doses of 100 to 1000 mg/body/day, usually once a week or every 3 to 4 weeks.

Presently preferred and practical embodiments of the present invention are illustratively shown in the following Examples.

EXAMPLE 1

(Ammine)(1,1-cyclobutanedicarboxylato)(pyrrolidine) platinum (II) 5

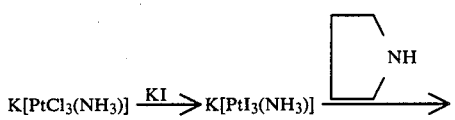

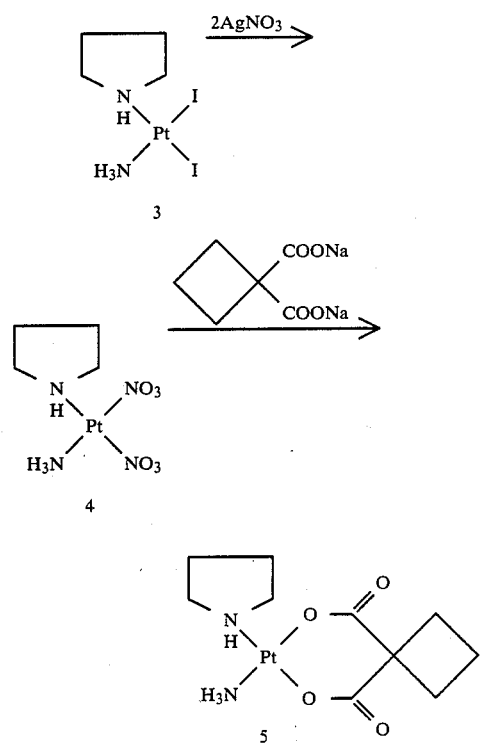

(a): (Ammine)(cis-diiodo)(pyrrolidine)platinum (II) 3

To a mixture of 6.44 g (18.0 mmol) of Compound 1 in 30 ml of water was added an aqueous solution (120 ml) of 135 g (810 mmol) of KI, and the mixture was stirred at room temperature for 45 minutes. The mixture was mixed with an aqueous solution (5 ml) of 1.32 g (18.5 mmol) of pyrrolidine and stirred at room temperature for 45 minutes.

The resulting yellow solid material was collected by filtration, washed with cold water and dried at 60° C. in vaccum. The mother liquor was allowed to stand overnight to give 0.1 g of yellow solid.

Yield: 9.1 g (97%)

The product is a mixture of

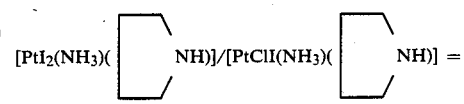

84/16 by weight.

m.p.: 110° C. ~ (decomp.)

Anal. Calcd. (%) for $C_4H_{12}N_2Cl_{0.19}I_{1.81}Pt$: : C,9.24; H,2.33; N,5.36; Pt,37.52. Found (%): C,9.21; H,2.33; N,5.36; Pt,37.37.

IR ν (Nujol): 3300 (m), 3270 (s), 3200 (s), 3050 (m), 1605 (m) 1350 (w), 1310 (w), 1280 (w), 1260 (S), 1125 (m) 1045 (m), 960 (w), 935 (w), 900 (m), 770 (w), 740 (m) cm$^{-1}$.

(b): (Ammine)(cis-dinitorato)(pyrrolidine)platinum (II) 4

The mixture of 8.6 g (16.6 mmol) of diiodo Compound 3 containing 16% by weight of

[PtClI(NH₃)(⌐NH⌐)],

EXAMPLE 2

(Ammine)(2-ethylmalonato)(pyrrolidine)platinum (II) 6

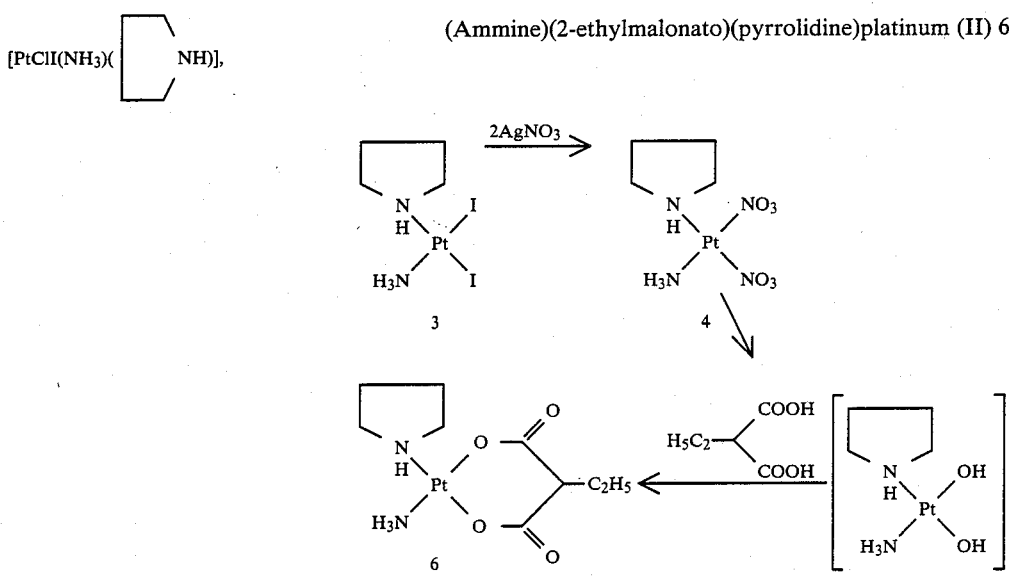

5.38 g (31.6 mmol) of AgNO₃ and 100 ml of water was stirred at room temperature for 16 hours under shielding light. The reaction mixture was filtered and washed with water. The residue was mixed with the filtrate and concentrated to give 140 g of an aqueous solution of Compound 4 (giving no turbidity by 1% potassium chloride). Then 4.37 g of the solution was concentrated at 50° C. and dried at 75° C. in vaccum until it gave a constant weight. Further 208 mg of Compound 4 was obtained as light yellow hygroscopic solid.

Yield: 100%

¹HMR: (δ, D₂O, ppm, TMS as external standard): 2.25 (b.m, $C_3$—$H_2$, $C_4$—$H_2$); 3.15* (bm, $C_2$—$H_A$, $C_5$—$H_A$); 3.65* (bm, $C_2$—$H_B$, $C_5$—$H_B$); 6.40 (vb, NH, NH₃).

(*: $J_{195}$ Pt-H couldn't read because of broadness.)

(c): (Ammine)(1,1-cyclobutanedicarboxylato)(pyrrolidine)platinum (II) 5

To 55 ml of an aqueous solution 9.09 mmol of dinitlato Complex 4 was added 1.31 g (9.09 mmol) of 1,1-cyclobutanedicarboxylic acid, and the resultant solution was adjusted to pH 7 with aqueous sodium hydroxide. After stirring at room temperature for 1 hour, the mixture was concentrated under reduced pressure, and the precipitated solid was filtered and recrystallized from water to give 4.0 g of Compound 5.

Yield: 80.1% m.p.: 205° C. ~(decomp.)

Anal. Calcd. (%) for $C_{10}H_{18}N_2O_4Pt$ : C, 28.24; H, 4.27; N, 6.59; Pt, 45.87. Found (%): C, 28.18; H, 4.22; N, 6.68; Pt, 45.65.

IR ν (Nujol): 3400 (b, m); 3250 (s); 3190 (s); 3150 (s); 1640 (s); 1610 (s); 1580 (s); 1320 (w); 1290 (w); 1250 (w); 1220 (w); 1170 (w); 1120 (sh); 1110 (m); 1040 (w); 1010 (w); 950 (w); 905 (m); 860 (w); 780 (m); 750 (w); 700 (w) cm⁻¹.

¹HNMR: (δ, D₂O, ppm, TMS as external standard,) 1.93–2.55 (m, $C_3$—$H_2$, $C_4$—$H_2$ in pyrrolidine, $C_3$—$H_2$ in cyclobutane); 3.33 (t, $C_2$—$H_2$, $C_4$—$H_2$ in cyclobutane); 2.86–3.89 (m, $C_2$—$H_2$, $C_5$—$H_2$ in pyrrolidine).

The solution (20 ml: containing 3.83 mmol of Compound 4) of dinitolato Compound 4 obtained in Example 1 was passed through a column of about 55 ml of Diaion SA-10A (OH⁻ type) as an anion exchange resin. The alkaline eluate was mixed with 505.8 mg (3.83 mmol) of ethylmalonic acid and stirred for 1 hr. The mixture was concentrated under reduced pressure and the precipitated solid was collected and recrystallized from water to give 461 mg of Compound 6 as white crystals.

Yield: 29.3% m.p.: 178° ~195° C. (decomp.)

Anal. Calcd. (%) for $C_4H_{18}N_2O_4Pt$. ($H_2O$) : C, 25.06; H, 4.67; N, 6.49; Pt, 45.23. Found (%): C, 24.74; H, 4.57; N, 6.63; Pt, 45.10.

IR ν (Nujol): 3580 (w); 3400 (m); 3280 (w); 3200 (w); 3140 (s); 2700 (b, w); 2200 (b, w); 1660 (sh); 1620 (s); 1600 (sh); 1420 (m); 1400 (s); 1370 (sh); 1340 (w); 1310 (w); 1235 (w); 1095 (w); 1030 (w); 980 (w); 950 (w); 905 (w); 830 (w); 810 (w); 760 (w) cm⁻¹.

¹HNMR: (δ, D₂O, ppm, TMS as external standard) 1.50 (t, J=7.5 Hz, CH₃); 3.06 (q, J=7.5 Hz, —CH₂—in ethyl); 3.93 (t, J=7.5 Hz, >CH—); 1.93–2.51 (m, $C_3$—$H_2$, $C_4$—$H_2$ in pyrrolidine); 2.80–3.40 (m, $C_2$—$H_A$, $C_5$—$H_A$ in pyrrolidine); 3.40–3.83 (m, $C_2$—$H_B$, $C_5$—$H_B$ in pyrrolidine).

EXAMPLE 3

(Ammine)(oxalato)(pyrrolidine)platinum(II) 7

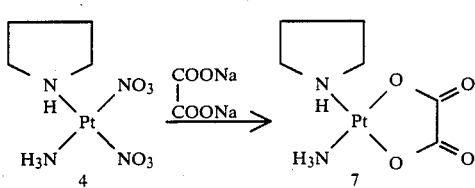

To the solution of 14 ml of dinitorato Complex 4 (equivalent to 1.60 mmol of Compound 4) obtained in Example 1 was added 214 mg (1.60 mmol) of sodium oxalate and the resultant solution was stirred at room temperature for 15 minutes and kept overnight. The resulting crystals was filtered and recrystallized from water to give 476 mg of Compound 7.

Yield: 73.0%.

m.p.: 194°~198° C. (decomp.).

Anal. Calcd. (%) for C<sub>6</sub>H<sub>12</sub>N<sub>2</sub>O<sub>4</sub>Pt. (H<sub>2</sub>O)<sub>2</sub> : C, 17.69; H, 3.96; N, 6.88; Pt, 47.90. Found (%): C, 17.98; H, 3.91; N, 6.98; Pt, 48.11.

IR ν (Nujol): 3500 (s); 3400 (sh); 3250 (sh); 3150 (s); 1690 (s); 1670 (s); 1400 (s); 1330 (w); 1260 (m); 1170 (b, w); 1050 (w); 900 (m); 800 (s) cm$^{-1}$.

EXAMPLE 4

(Ammine)(cis-dichloro)(pyrrolidine)platinum (II) 8

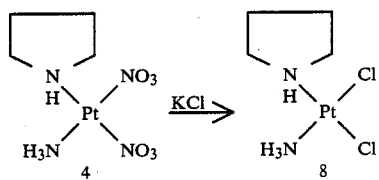

Aqueous solution (43.7 g) of dinitrato Complex 4 (containing 5.0 mmol of Complex 4) was concentrated to 20 ml, mixed with 6 ml of 20% aqueous potassium chloride and allowed to react at 50° C. for 30 minutes. After ice-cooling, the precipitated pale yellow crystals of Compound 8 were filtered.

Yield: 1.59 g, 90% m.p.: 180° C.~ (decomp.).

Anal. Calcd. (%) for C<sub>4</sub>H<sub>12</sub>N<sub>2</sub>Cl<sub>2</sub>Pt : C, 13.57; H, 3.42; N, 7.91; Cl, 20.02; Pt, 55.09. Found (%): C, 13.69; H, 3.58; N, 7.86; Cl, 19.76; Pt, 54.34.

IR ν (Nujol): 3270 (m); 3175 (s); 1630 (bw); 1550 (bw); 1320 (w); 1300 (m); 1290 (sh); 1230 (w); 1175 (w); 1055 (m); 920 (sh); 910 (m); 900 (w); 820 (w) cm$^{-1}$.

EXAMPLE 5

(Ammine)(glycolato-0,0′)(pyrrolidine)platinum (II) 10a, 10b

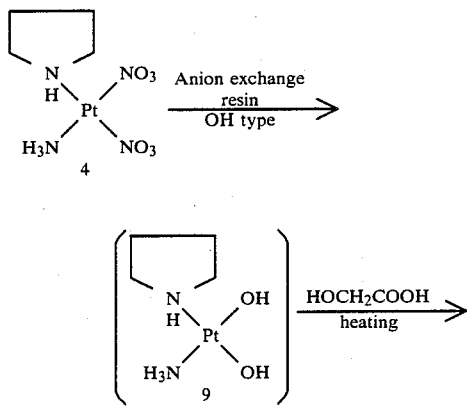

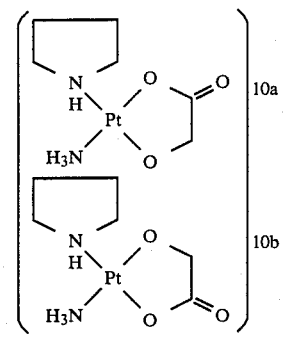

(10a and 10b were isomers each other, but the correspondance to the structure was not elucidated.)

To the solution of 91.9 g of dinitrato Compound 4 (containing 10.5 mmol of Complex 4) was concentrated to 30 ml and passed through 70 ml of a column of Diaion SA-10A (OH-type) as an anion exchange resin to give 105 ml of the solution of Compound 9.

To the solution were added 799 mg (10.5 mmol) of glycolic acid and 2.1 g (21 mmol) of sodium glycolate and the mixture was heated at 60° C. for 1 hour. After the reaction solution was adjusted to pH 7.4, it was further heated for 5 hours.

The resulting solution was concentrated, and the residue was mixed with 50 ml of methanol, heated for a short time and the insoluble material was removed.

The methanolic solution was concentrated to 20 ml and passed through a column of silica gel and the eluate of which the Rf values were 0.42 (10a) and 0.30 (10b) on a thin layer chromatography (hereinafter abbreviated as "TLC") was collected. The eluate was passed through the Lobar column to separate each component and then 1.35 g of crude crystals of 10a and 1.40 g of crude crystals of 10b were obtained. The crude crystals of 10a was recrystallized from methanol-acetone and dried at 90° C. in vacuum for 6 hours to give 1.15 g of the pure 10a as pale yellow crystals containing 0.3 mol equivalent of methanol. (Yield: 30%)

In the same method, the crude 10b was recrystallized from methanol and dried at 90° C. in vaccum for 6 hours to give 1.28 g of the pure 10b as pale yellow crystals. (Yield: 34%) Isomer 10a (Rf=0.42); m.p.: 155°~185° C. (decomp.)

Anal Calcd. (%) for C<sub>6</sub>H<sub>14</sub>N<sub>2</sub>O<sub>3</sub>Pt (CH<sub>3</sub>OH)<sub>0.3</sub> : C, 20.62; H, 4.17; N, 7.60; Pt, 53.16. Found (%): C, 19.94; H, 4.24; N, 7.53; Pt, 52.66.

IR ν (Nujol): 3550 (sh); 3200 (bs); 3100 (bm); 1635 (s); 1610 (s); 1350 (s); 1305 (m); 1055 (m); 1050 (m); 920 (m); 900 (w); 865 (w); 760 (w); 715 (w) cm$^{-1}$.

$^1$HNMR: (δ, D<sub>2</sub>O, ppm, TMS as external standard) 2.23 (bm, C<sub>3</sub>—H<sub>2</sub>, C<sub>4</sub>—H<sub>2</sub>); 3.15 (bm, C<sub>2</sub>—H<sub>A</sub>, C<sub>5</sub>—H<sub>A</sub>); 3.60 (bm, C<sub>2</sub>—H<sub>B</sub>, C<sub>5</sub>—H<sub>B</sub>); 3.80 (s, MeOH); 4.53 (s, J<sub>195Pt-H</sub>=36.0 Hz, glyclato CH<sub>2</sub>).

Isomer 10b (Rf=0.30); m.p.: 209°~212° C. (decomp.).

Anal Calcd. (%) for C<sub>5</sub>H<sub>14</sub>N<sub>2</sub>O<sub>3</sub>Pt : C, 20.17; H, 3.95; N, 7.84; Pt, 54.60. Found (%): C, 20.01; H, 3.89; N, 7.79; Pt, 55.00.

IR ν (Nujol): 3250 (m); 3160 (s); 1625 (s); 1600 (s); 1360 (s); 1340 (s); 1310 (m); 1220 (w); 1175 (w); 1065 (s); 1040 (m); 930 (m); 920 (m); 905 (m); 890 (w); 860 (w); 760 (w) cm$^{-1}$.

¹HNMR: (δ, D₂O, ppm, TMS as external standard) 2.24 (bm, C₃—H₂, C₄—H₂); 3.23 (bm, C₂—H_A); 3.64 (bm, C₂—H_B, C₅—H_B); 4.57 (s, J₁₉₅pt-H=31.5 Hz, glycolto CH₂)

EXAMPLE 6

(Ammine)(1,1-cyclobutanedicarboxyrato)(piperidine)-platinum (II) 13

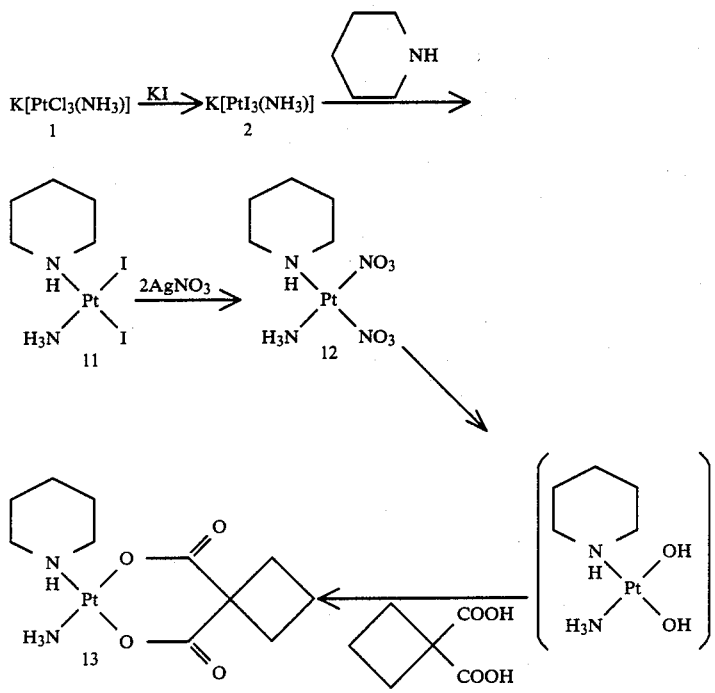

(a) (Ammine)(cis-diiodo)(piperidine)platinum (II) 11

Using 5.36 g of Compound 1, the reaction was performed in the same method as in Example 1-(a), whereby 8.70 g of the mixture of

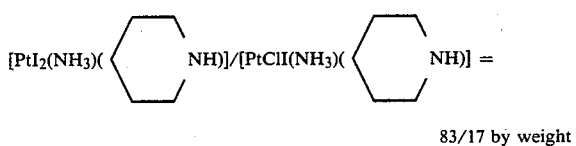

83/17 by weight was obtained.
Yield: 97%.
m.p.: 110° C. ~ (decomp.).
Anal. Calcd. (%) for C₅H₁₄N₂Cl₀.₂₀I₁.₈₀Pt : C, 11.27; H, 2.65; N, 5.25; Pt, 36.60. Found (%): C, 11.45; H, 2.68; N, 5.10; Pt, 36.31.

(b) (Ammine)(cis-diniorato)(piperidine) platinum (II) 12

6.50 g (11.8 mmol) of Compound 11 was reacted in the same method as in Example 1-(b) to give 118 g of an aqueous solution containing 11.5 mmol of Compound 12. The solution (5.0 g) was concentrated and dried in vacuum to give 209 mg of pale yellow glassy solid.
Yield: 99%
¹HNMR: (δ, D₂O, ppm, TMS as external standard) 2.05 (bm, C₃—H₂, C₄—H₂, C₅—H₂); 3.25* (bm, C₂—H_A, C₆—H_A); 3.73 (C₂—H_B, C₅—H_B); 6.20 (vb, NH, NH₃).
(*: J₁₉₅ Pt-H could not read because of broadness)

(c) (Ammine)(1,1-cyclobutanedicarboxylato)(piperidine)platinum (II) 13

The solution containing 3.26 mmol of Compound 12 (30 ml) was passed through a column of Diaion SA-10A (OH⁻ type). To the eluate was added 467.4 mg (3.24 mmol) of 1,1-cyclobutanedicarboxylic acid. The resulting solution was stirred for 0.5 hr. at room temperature and concentrated to give 1.21 g of Compound 13 as crystals.
Yield: 81.5%.
m.p.: 200° C. ~ (decomp.).
Anal. Calcd. (%) for C₁₁H₂₀N₂O₄Pt : C, 28.89; H, 4.85; N, 6.12; Pt, 42.65. Found (%): C, 28.93; H, 4.91; N, 6.27; Pt, 42.73.
IR ν (Nujol): 3500 (m); 3450 (sh); 3250 (m); 3170 (sh); 3140 (m); 3100 (sh); 1630 (s); 1600 (s); 1580 (sh); 1570 (sh); 1550 (sh); 1540 (sh); 1445 (m); 1415 (sh); 1360 (s); 1310 (w); 1280 (w); 1240 (w); 1230 (m); 1215 (w); 1130 (w); 1110 (m); 1070 (w); 1020 (w); 940 (w); 890 (m); 855 (m); 805 (w); 770 (w); 750 (w) cm⁻¹.
¹HNMR: (δ, D₂O, ppm, TMS as external standard) 2.03 (bm, C₃—H₂, C₄—H₂, C₅—H₂ in piperidine); 2.34 (q, C₃—H₂ in cyclobutane); 3.33 (t, C₂—H₂, C₄—H₂ in cyclobutane); 2.96-3.51 (bm, C₂—H_A, C₆—H_A in piperidine); 3.51-4.04 (bm, C₂—H_B, C₆—H_B in piperidine).

EXAMPLE 7

(Ammine)(2-ethylmalonato)(piperidine)platinum (II) 14

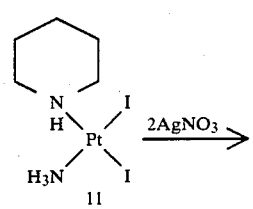

-continued

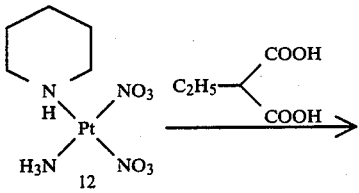

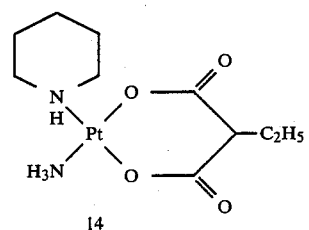

To 25 ml of the solution of dinitorato Compound 12 (containing 3.6 mmol of Compound 12) obtained in Example 6 was added 502.4 mg (3.80 mmol) of ethylmalonic acid, and the solution was adjusted to pH=7 with 10% NaOH, and the resultant solution was reacted at room temperature for about 1 hour. After concentration at 50° C., the oily residue was subjected to a column of silica gel for purification. The eluate of Rf=0.66 was collected. The eluate was concentrated and recrystallized from water to give 826.9 mg of Compound 14.

Yield: 51.6%.

m.p.: 188° C.~ (decomp.).

Anal. Calcd. (%) for $C_{10}H_{20}N_2O_4Pt \cdot H_2O$ : C, 26.97; H, 4.98; N, 6.29; Pt, 43.80. Found (%): C, 26.68; H, 4.90; N, 6.37; Pt, 43.90.

IR $\nu$ (Nujol): 3400 (m); 3280 (m); 3200 (sh); 3100 (m); 1615 (s); 1590 (s); 1405 (s); 1385 (s); 1360 (sh); 1330 (w); 1300 (w); 1230 (w); 1190 (w); 1140 (w); 1085 (w); 1020 (w); 970 (w); 940 (w); 880 (w); 860 (w); 830 (w); 815 (sh); 805 (sh); 760 (w); 695 (w) cm$^{-1}$.

$^1$HNMR: ($\delta$, D$_2$O, ppm TMS as external standard) 1.50 (t, J=7.5 Hz, —CH$_3$); 2.06 (bm, C$_3$—H$_2$, C$_5$—H$_2$ in piperidine); 3.07 (d, q, (d)J=9, (q)J=7.5, —CH$_2$—in ethyl); 2.75–3.50 (bm, C$_2$—H$_A$, C$_6$—H$_A$ in piperidine); 3.50–3.96 (bm, C$_2$—H$_B$, C$_6$—H$_B$ in piperidine).

EXAMPLE 8

(Ammine)(oxalato)(piperidine)platinum (II) 15

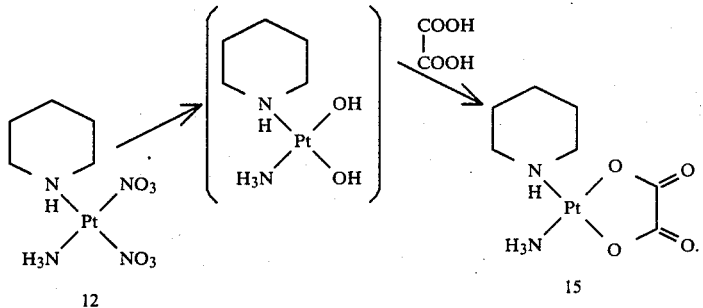

The solution (15 ml) of dinitrato Compound 12 (containing 1.80 mmol of Compound 12) obtained in Example 6 was passed through a column of about 25 ml of Diaion SA-10A (OH type) as an anion exchange resin. The alkaline eluate was collected, mixed with 222 mg (1.76 mmol) of oxalic acid and reacted at room temperature for 1.5 hours. The resulting solid was recrystallized from water to give 535.7 mg of Compound 15. (Yield: 77.2%).

m.p.: 225° C.~(decomp.).

Anal. Calcd. (%) for $C_7H_{14}N_2O_4Pt$: C, 21.82; H, 3.66; N, 7.27; Pt, 50.63. Found (%): C, 21.47; H, 3.77; N, 7.23; Pt, 50.29.

IR $\nu$ (Nujol): 3450 (b, w); 3270 (sh); 3230 (m); 3175 (m); 3100 (m); 2450 (w); 2200 (w); 1685 (s); 1670 (sh); 1650 (s); 1590 (sh); 1450 (sh); 1375 (s); 1350 (sh); 1335 (m); 1315 (w); 1275 (w); 1240 (m); 1230 (sh); 1140 (w); 1105 (w); 1025 (w); 1010 (w); 940 (m); 865 (m); 850 (m); 800 (s) cm$^{-1}$.

EXAMPLE 9

(Ammine)(cis-dichloro)(piperidine)platinum (II) 16

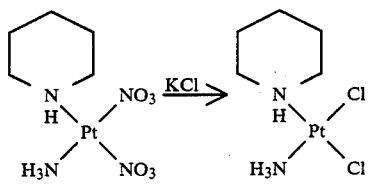

Using 13.0 g of an aqueous solution of dinitrato Compound 12 (containing 1.3 mmol of Compound 12), the reaction was performed in the same method as in Example 4, whereby 430 mg of the Compound 16 was obtained as pale yellow crystals.

Yield: 90% m.p.: 190° C.~(decomp.).

Anal. Calcd. (%) for $C_5H_{14}N_2Cl_2Pt$: C, 16.31; H, 3.83; N, 7.61; Cl, 19.26; Pt, 52.98. Found (%): C, 16.44; H, 3.80; N, 7.60; Cl, 19.55; Pt, 53.01.

IR $\nu$ (Nujol): 3260 (m); 3200 (s); 3175 (s); 1640 (m); 1595 (w); 1550 (m); 1350 (m); 1330 (m); 1315 (s); 1280 (w); 1225 (w); 1200 (w); 1135 (w); 1080 (w); 1035 (m); 1020 (w); 860 (w); 820 (m); 785 (w) cm$^{-1}$.

EXAMPLE 10

(Ammine)(glycolato-O,O')(piperidine)platinum (II) 18a, 18b

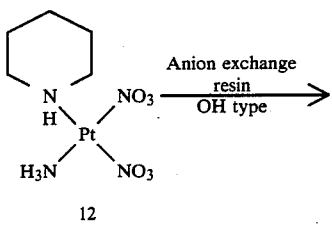

12

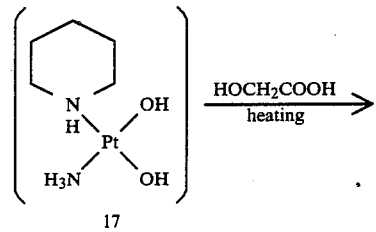

17

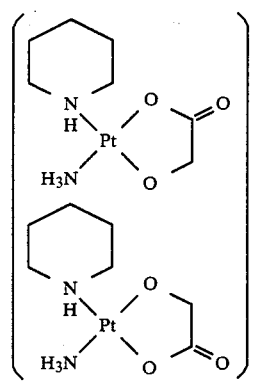

18a

18b (18a and 18b were isomers each other, but the correspondance to the structure was not elucidated.)

Using 100 g of an aqueous solution of dinitrato Compound 4 (containing 10 mmol of Compound 4), the reaction was performed in the same method as in Example 5, and the reaction mixture was recrystallized from methanol/acetone=1/10 by weight to give 0.75 g of Compound 18a as pale yellow crystals.

Yield: 20%. Similarly the crude 18b was recrystallized from methanol to give 1.28 g of Compound 18b as pale yellow crystals.

Yield: 35%.

Isomer 18a (Rf=0.45); m.p.: 180°~190° C. (decomp.).

Anal. Calcd. (%) for $C_7H_{16}N_2O_3Pt$: C, 22.64; H, 4.34; N, 7.54; Pt, 52.54. Found (%): C, 22.21; H, 4.47; N, 7.64; Pt, 51.82.

IR $\nu$ (Nujol): 3250 (sh); 3160 (bm); 3070 (bm); 1635 (s); 1610 (s); 1340 (s); 1300 (s); 1275 (w); 1220 (w); 1190 (w); 1130 (w); 1080 (m); 1040 (m); 1030 (w); 1005 (w); 935 (w); 875 (w); 850 (w); 750 (w); 715 (w) cm$^{-1}$.

$^1$HNMR: ($\delta$, $D_2O$, ppm, TMS as external standard) 2.03 (bm, $C_3$—$H_2$, $C_4$—$H_2$, $C_5$—$H_2$); 3.20 (bm, $C_2$—$H_A$, $C_5$—$H_A$); 3.70 (bm, $C_2$—$H_B$, $C_6$—$H_B$); 4.53 (s, $J_{195Pt-H}$=36 Hz, glycolato $CH_2$). Isomer 18b (Rf=0.34); m.p.: 190°~215° C. (decomp.).

Anal. Calcd. (%) for $C_7H_{16}N_2O_3Pt$: C, 22.64; H, 4.34; N, 7.54; Pt, 52.54. Found (%): C, 22.51; H, 4.24; N, 7.57; Pt, 52.47.

IR $\nu$ (Nujol): 3260 (m); 3210 (m); 3170 (s); 1620 (s); 1595 (s); 1350 (s); 1325 (m); 1310 (m); 1270 (w); 1220 (w); 1130 (w); 1100 (w); 1070 (m); 1030 (w); 1020 (w); 930 (w); 920 (w); 910 (w); 860 (m); 810 (w); 755 (m); 715 (w) cm$^{-1}$.

$^1$HNMR: ($\delta$, $D_2O$, ppm, TMS as external standard) 2.03 (bm, $C_3$—$H_2$, $C_4$—$H_2$, $C_5$—$H_2$); 3.25 (bm, $C_2$—$H_A$, $C_6$—$H_A$); 3.70 (bm, $C_2$—$H_B$, $C_6$—$H_B$); 4.53 (s, $J_{195Pt-H}$=31.5 Hz, glycolato $CH_2$).

EXAMPLE 11

(Ammine)(cis-dichloro)(4-piperidone)platinum (II) 21

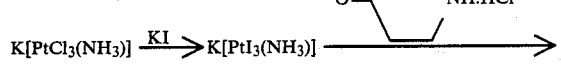

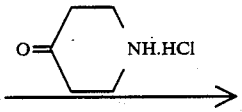

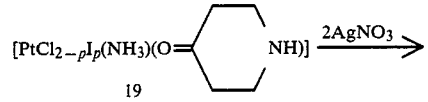

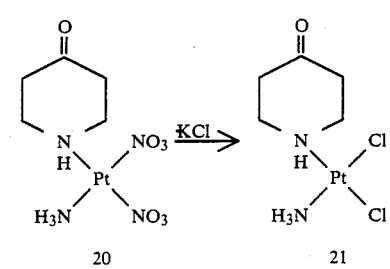

20   21

(wherein p is an integer of 1 or 2.)

(a) The mixture 19 consisting of (ammine)(cis-chloroiodo)(4-piperidone)platinum (II), (ammine)(cis-diiodo)(4-piperidone)platinum (II)

To 716 mg (2.0 mmol) of Compound 1 in 7.5 ml of water was added 1.99 g (12.0 mmol) of KI to give a red solution. It was mixed with 360 mg (2.00 mmol) of 4-piperidone hydrochloride (97%) and then 2.0 ml of 1N NaOH to give pale yellow solid. The resulting mixture was stirred at room temperature under shielding light for 2 hours. The precipitate was filtered, washed successively with water, ethanol and ether and dried at 60° C. in vacuum to give 830 mg of the desired mixture 19 as pale yellow solid, which was presumed to include

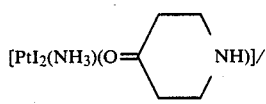

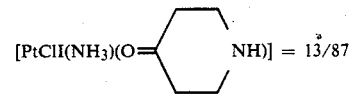  = 13/87 by weight from the elemental analysis of Pt.

Yield: 86%.

m.p.: 165° C. ~(decomp.).

Anal. Calcd. (%) for $C_5H_{12}N_2OCl_{0.89}I_{1.11}Pt$: C, 12.42; H, 2.50; N, 5.79; Pt, 40.33. Found (%): C, 12.32; H, 2.50; N, 5.70; Pt, 40.29.

IR $\nu$ (Nujol): 3460 (w); 3240 (m); 3160 (s); 1720 (s); 1690 (w); 1550 (w); 1405 (w); 1330 (m); 1300 (m); 1195 (m); 1180 (w); 1105 (w); 1090 (w); 1005 (w); 980 (w); 945 (w); 850 (w); 765 (w) cm$^{-1}$.

(b) (Ammine)(cis-dinitrato)(4-piperidone)platinum (II) 20

A mixture of 1.12 g (2.31 mmol) of the compound 19, 769 mg (4.52 mmol) of AgNO$_3$ and 20 ml of water was stirred at room temperature for 8 hours with shielding light and filtered. The filtrate was concentrated under reduced pressure and dried in vacuum for 6 hours to give 997 mg of the objective compound.

NMR: ($\delta$, D$_2$O, ppm, TMS as external standard) 2.0–4.3 (m, C$_2$H$_2$, C$_3$H$_2$, C$_5$H$_2$, C$_6$H$_2$); 4.2–5.8 (Vb, NH$_3$); 5.7–7.4 (NH, J$_{195Pt-H}$=48 Hz).

(c) (Ammine)(cis-dichloro)(4-piperidone)platinum (II) 21

To a solution of 947 mg (2.18 mmol) of Compound 20 in 4 ml of water was added 3 ml of an aqueous solution including a slightly more than 2 mol equivalent of KCl and heated at 50° C. to give a pale yellow precipitate. Further the mixture was heated for 10 minutes and allowed to stand at room temperature for 1 hour. After cooling, the precipitated solid was collected by filtration. The collected solid was dissolved in 50 ml of 1% KCl solution under heating, concentrated to 5 ml under reduced pressure and the precipitated pale yellow crystals were filtered. The crystals were washed with a small amount of water and dried at 60° C. in vacuum to give 605 mg of the objective Compound 21.

Yield: 72%.

m.p.: 195° C.~(decomp.).

Anal. Calcd. (%) for $C_5H_{12}N_2Cl_2OPt$: C, 15.71; H, 3.17; N, 7.33; Cl, 18.55; Pt, 51.04. Found (%): C, 15.48; H, 3.14; N, 7.32; Cl, 18.51; Pt, 50.89.

IR $\nu$ (Nujol): 3400 (w); 3270 (m); 3160 (m); 3100 (sh); 1718 (s); 1570 (w); 1305 (m); 1286 (m); 1190 (m); 1110 (w); 1090 (w); 1010 (w); 980 (w); 940 (w); 850 (w); 830 (w); 760 (w) cm$^{-1}$.

EXAMPLE 12

(Ammine)(cis-dichloro)(3-hydroxypyrrolidine)platinum (II) 24

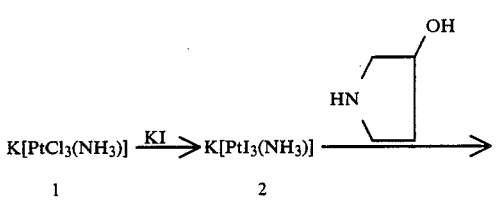

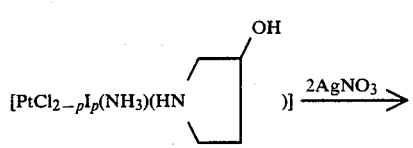

(wherein p is an integer of 1 or 2.)

(a) The mixture 22 consisting of (ammine)(cis-chloroiodo)(3-hydroxypyrrolidine)platinum (II) and (ammine)(cis-diiodo)(3-hydroxypyrrolidine)platinum (II)

To a solution of 1.44 g (4.02 mmol) of Compound 1 in 15 ml of water was added 4.01 g (24.2 mmol) of KI and the mixture was stirred at room temperature for 30 minutes with a shielding of light, mixed with a solution of 0.371 g (4.02 mmol) of 3-pyrrolidinol in 3 ml of water and allowed to stand overnight at room temperature. The precipitate was filtered, washed succesively with water, ethanol and ether and dried at 40° C. in vacuum to give 1.55 g of the desired mixture 22 as a yellow precipitate, which was presumed to include

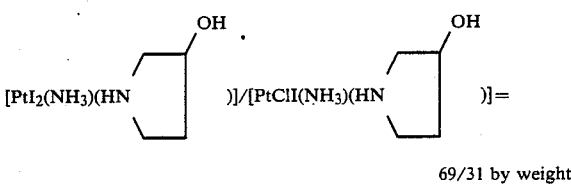

69/31 by weight from the elemental analysis of Pt.

Yield: 74%.

m.p.: 115° C.~(decomp.).

Anal. Calcd. (%) for $C_4H_{12}N_2OCl_{0.35}I_{1.65}Pt$: C, 9.25; H, 2.40; N, 5.29; Pt, 37.27. Found (%): C, 9.22; H, 2.32; N, 5.38; Pt, 37.44.

IR $\nu$ (Nujol): 3450 (s); 3275 (m); 3200 (s); 3090 (m); 1640 (w); 1395 (w); 1340 (m); 1320 (m); 1285 (m); 1245 (w); 1225 (w); 1180 (w); 1115 (m); 1080 (m); 1040 (w); 1020 (w); 980 (m); 955 (w); 905 (w); 880 (m); 850 (w); 835 (w); 750 (w) cm$^{-1}$.

(b) (Ammine)(cis-dinitrato)(3-hydroxypyrrolidine)platinum (II) 23

A mixture of 1.35 g (2.59 mmol) of Compound 22 and 863 mg (5.08 mmol) of AgNO$_3$ in 25 ml of water was stirred at room temperature for 8 hours with a shielding of light and filtered. The filtrate was mixed with several drops of 1% KCl and a very small amount of white precipitate was filtered off. The mixture was concentrated under reduced pressure and the residue was dried at 40° C. in vacuum for 6 hours to give 1.07 g of Compound 23.

Yield: 99%.

NMR: ($\delta$, D$_2$O, ppm, TMS as external standard) 2.2–2.8 (m, C$_4$H$_2$); 3.1–4.0 (m, C$_2$H$_2$, C$_5$H$_2$); 4.90 (m, CH$_3$); 4.0–6.0 (Vb, NH$_3$); 6.0–7.7 (Vbt, NH, J$_{195Pt-H}$=48 Hz).

(c) (Ammine)(cis-dichloro)(3-hydroxypyrrolidine)platinum (II) 24

To a solution of 1.05 g (2.48 mmol) of the Compound 23 in 4 ml of water were added 0.45 g (6.0 mmol) of KCl and 3 ml of water and the mixture was heated at 50° C. for a few minutes to give a pale yellow solid as a precip-

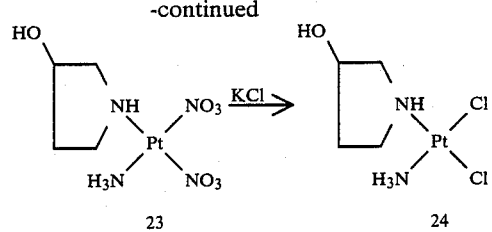

itate. The solution was heated for 10 minutes further allowed to stand for 1 hour at room temperature and cooled with water to give a precipitate. The precipitate was dissolved in 50 ml of 1% KCl under heating, concentrated to 5 ml under reduced pressure and pale yellow crystals were filtered. The crystals were washed with a small amount of water and dried at 60° C. in vacuum to give 670 mg of Compound 24.

Yield: 73%.

m.p.: 177°–179° C.

Anal. Calcd. (%) for $C_4H_{12}N_2Cl_2OPt$: C, 12.98; H, 3.27; N, 7.57; Cl, 19.16; Pt, 52.71. Found (%): C, 12.73; H, 3.15; N, 7.59; Cl, 18.93; Pt, 52.71.

IR $\nu$ (Nujol): 3450 (s); 3275 (m); 3210 (m); 3100 (m); 1570 (w); 1350 (m); 1330 (m); 1295 (w); 1260 (w); 1240 (m); 1190 (w); 1020 (m); 1080 (m); 1025 (w); 990 (w); 960 (w); 885 (m); 855 (w); 845 (w); 810 (w); 760 (w) cm$^{-1}$.

EFFECT OF THE INVENTION

The objective compounds (I) of the present invention have higher water-solubility than other platinum complexes cited herein and show potent antitumor activities; particularly the compounds (I) show outstanding antitumor activities against Murine Leukemia L1210 resistant to cisplatin (hereinafter abbreviated as L1210/CDDP) and Walker Carcinosarcoma 256.

The antitumor activity of the objective compounds of the present invention will be explained by the following Experiments.

EXPERIMENT 1

Antitumor activity against Murine Leukemia L 1210 resistant to cisplatin (Test method)

Murine Leukemia L 1210 ascites cells ($10^5$ cells) were intraperitoneally inoculated to $BDF_1$ mice, and next day a predetermined amount of the test compounds was administered intraperitoneally. The saline was used as a solvent for injection.

(Test compound)

(A) (Ammine)(cis-dichloro)(pyrrolidine)platinum (II) 8
(B) (Ammine)(glycolato-O,O')(pyrrolidine)platinum (II) 10a (Rf value: 0.42)
(C) (Ammine)(glycolato-O,O')(pyrrolidine)platinum (II) 10b
(D) (Ammine)(cis-dichloro)(piperidine)platinum (II) 16
(E) (Ammine)(glycolato-O,O')(piperidine)platinum (II) 18a (Rf value: 0.45)
(F) (Ammine)(glycolato-O,O')(piperidine)platinum (II) 18b (Rf value: 0.34)
(G) Cisplatin (CDDP)
(H) Carboplatin.

EVALUATION OF THE EFFECT

From the average survival days (a) in the test group and those (b) of the untreated control group, the increasing ratio of lifespan (ILS) was calculated according to the following formula.

$$ILS (\%) = \frac{(a) - (b)}{(b)} \times 100$$

A curative index CI was determined from a dosage showing 30% increasing ratio of lifespan ($ILS_{30}$) and that showing the maximal increasing ratio of lifespan ($ILS_{max}$).

$$CI = \frac{ILS_{MAX}}{ILS_{30}}$$

The larger the CI value is, the more effective the compound is. The results are shown in Table 1.

EXAMPLE 2

Antitumor Activity against Walker Carcinosarcoma 256

(Test Method)

The tumor seed of Walker Carcinosarcoma was subcutaneously inoculated to Wistar rats (4 weeks of the age, female) and a predetermined amount of the test compound was intravenously administered for 5 days continuously from the next day of the inoculation. Saline was used as a solvent for injection.

(Test compound)

(A) (Ammine)(cis-dichloro)(pyrrolidine)platinum (II) 8
(B) (Ammine)(glycolato-O,O')(pyrrolidine)platinum (II) 10a (Rf value: 0.42)
(C) (Ammine)(glycolato-O,O')(pyrrolidine)platinum (II) 10b
(D) (Ammine)(cis-dichloro)(piperidine)platinum (II) 16
(E) (Ammine)(glycolato-O,O')(piperidine)platinum (II) 18a (Rf value: 0.45)
(F) (Ammine)(glycolato-O,O')(piperidine)platinum (II) 18b (Rf value: 0.34)
(G) Cisplatin (CDDP)
(H) Carboplatin.

(Evalution of the Effect)

From the average survival days (a) in each test group and those (b) of the untreated control group, the increasing ratio of lifespan (ILS) was calculated according to the following formula.

$$ILS (\%) = \frac{(a) - (b)}{(b)} \times 100$$

A curative index CI was determined in the same manner as in Experiment 1. The results are shown in Table 2.

TABLE 1

| Comparison of antitumoractivity against to L1210/CDDP (CI value) | | | | | | | | |
|---|---|---|---|---|---|---|---|---|
| Compound | (A) | (B) | (C) | (D) | (E) | (F) | (G) | (H) |
| $ILS_{30}$ (mg/kg) | 0.7 | 1.25 | 13.5 | 0.65 | 1.35 | 3.0 | * | 10.0 |
| $ILS_{MAX}$ (mg/kg) | 10.0 | 20.0 | 40.0 | 10.0 | 40.0 | 40.0 | * | 133.0 |
| CI | 14.3 | 16.0 | 3.0 | 15.4 | 29.6 | 13.3 | * | 13.0 |
| Water solubility (mg/ml, room temperature) | 3.0 | >500 | >500 | 2.0 | >500 | >500 | 1.40 | 16.0 |

*means inefficiency

TABLE 2

Comparison of antitumor against Walker Carcinosarcoma 256 (CI value)

| Compound | (A) | (B) | (C) | (D) | (E) | (F) | (G) | (H) |
|---|---|---|---|---|---|---|---|---|
| $ILS_{30}$ (mg/kg) | 5.20 | 4.30 | 4.7 | 5.6 | 5.20 | 5.40 | 1.60 | 9.40 |
| $ILS_{MAX}$ (mg/kg) | 20.0 | 40.0 | 40.0 | 20.0 | 40.0 | 40.0 | 5.0 | 50.0 |
| CI | 3.80 | 9.30 | 8.50 | 3.60 | 7.70 | 7.40 | 3.1 | 5.3 |

What we claim is:

1. A compound which is (ammine)(glyccolato-O,O')-(pyrrolidine)platinum (II).
2. A compound which is (ammine)(glycolato-O,O')-(piperidine)platinum (II).

* * * * *